(12) United States Patent
Starke et al.

(10) Patent No.: US 10,617,877 B2
(45) Date of Patent: Apr. 14, 2020

(54) ELECTROMEDICAL IMPLANT COMPRISING AN ELECTRICAL FEEDTHROUGH

(71) Applicant: BIOTRONIK SE & Co. KG, Berlin (DE)

(72) Inventors: Marcel Starke, Eichwalde (DE); Jan Romberg, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 194 days.

(21) Appl. No.: 15/656,365

(22) Filed: Jul. 21, 2017

(65) Prior Publication Data

US 2018/0028821 A1 Feb. 1, 2018

(30) Foreign Application Priority Data

Aug. 1, 2016 (DE) .................... 10 2016 114 155

(51) Int. Cl.
*A61N 1/375* (2006.01)
*A61N 1/36* (2006.01)
(Continued)

(52) U.S. Cl.
CPC .......... *A61N 1/3754* (2013.01); *A61B 5/042* (2013.01); *A61B 5/076* (2013.01); *A61B 5/686* (2013.01);
(Continued)

(58) Field of Classification Search
CPC .............. A61N 1/3754; A61N 1/36062; A61N 1/39622; A61N 1/37512; A61N 1/37514
See application file for complete search history.

(56) References Cited

U.S. PATENT DOCUMENTS

2011/0077708 A1 3/2011 Ostroff
2012/0290021 A1* 11/2012 Saurkar .............. A61N 1/37205
607/2
(Continued)

FOREIGN PATENT DOCUMENTS

EP 0339877 A2 * 11/1989 ........... A61N 1/3752
EP 2 926 864 A1 10/2015

OTHER PUBLICATIONS

European Search Report dated Jan. 8, 2018 in European Application No. EP 17 18 3988.

*Primary Examiner* — Linda C Dvorak
*Assistant Examiner* — Annabeth E Rodriguez
(74) *Attorney, Agent, or Firm* — Buchanan Ingersoll & Rooney PC

(57) ABSTRACT

An electromedical implant, having a housing with three housing segments A, B and C. Segment A is joined to segment B, and segment B is joined to segment C, so that segment B is disposed between segments A and C. Segment A and segment C are at least partially made of electrically conducting material. Furthermore, an electronics module is disposed within housing segment A and has an electric circuit arrangement for picking up and further processing electrical signals, and at least one first and one second electrical conductor for measuring electrical potentials and/ or for delivering electric pulses. Each conductor has a conductor start and a conductor end, and each conductor start is connected to the electric circuit arrangement. An electrical feedthrough is at least partially made of electrically insulating material, and segment B is formed by portions of the feedthrough.

16 Claims, 7 Drawing Sheets

(51) Int. Cl.
*A61N 1/372* (2006.01)
*A61N 1/39* (2006.01)
*A61B 5/042* (2006.01)
*A61B 5/07* (2006.01)
*A61B 5/00* (2006.01)
*A61N 1/362* (2006.01)

(52) U.S. Cl.
CPC ........... *A61N 1/362* (2013.01); *A61N 1/3605* (2013.01); *A61N 1/36053* (2013.01); *A61N 1/36062* (2017.08); *A61N 1/375* (2013.01); *A61N 1/3756* (2013.01); *A61N 1/37217* (2013.01); *A61N 1/37229* (2013.01); *A61N 1/37512* (2017.08); *A61N 1/37514* (2017.08); *A61N 1/39622* (2017.08); *A61N 1/37205* (2013.01)

(56) References Cited

U.S. PATENT DOCUMENTS

| | | | |
|---|---|---|---|
| 2014/0058240 A1 | 2/2014 | Mothilal | |
| 2014/0100627 A1* | 4/2014 | Min | A61B 5/02158 607/32 |
| 2015/0073507 A1* | 3/2015 | Reinke | A61N 1/3787 607/61 |
| 2015/0283374 A1 | 10/2015 | Kronmueller et al. | |
| 2015/0321016 A1* | 11/2015 | O'Brien | A61N 1/3627 607/62 |

* cited by examiner

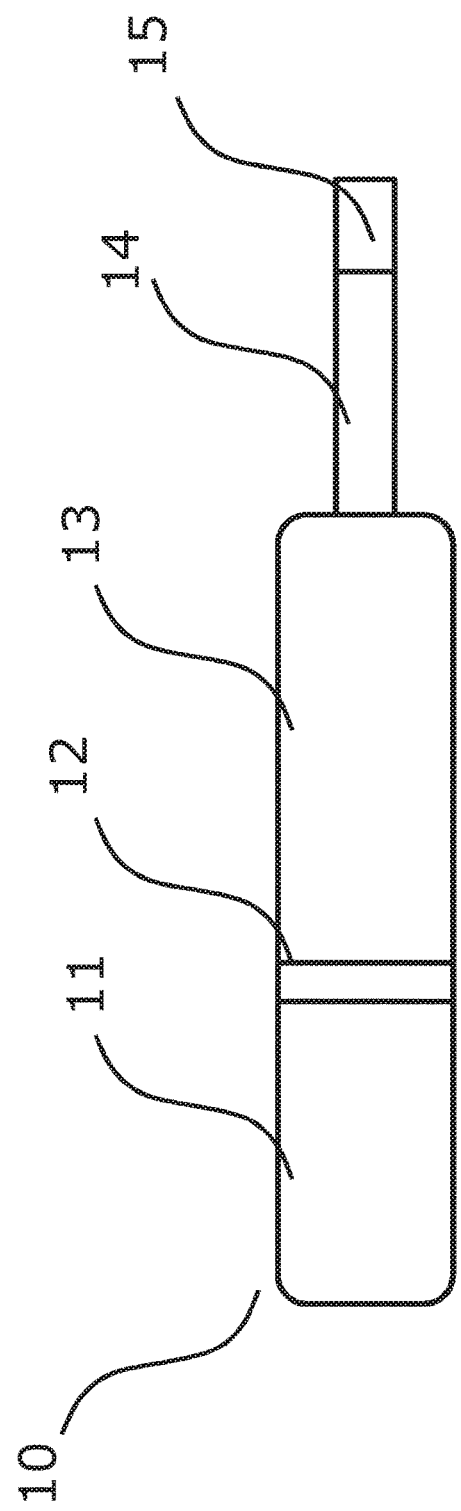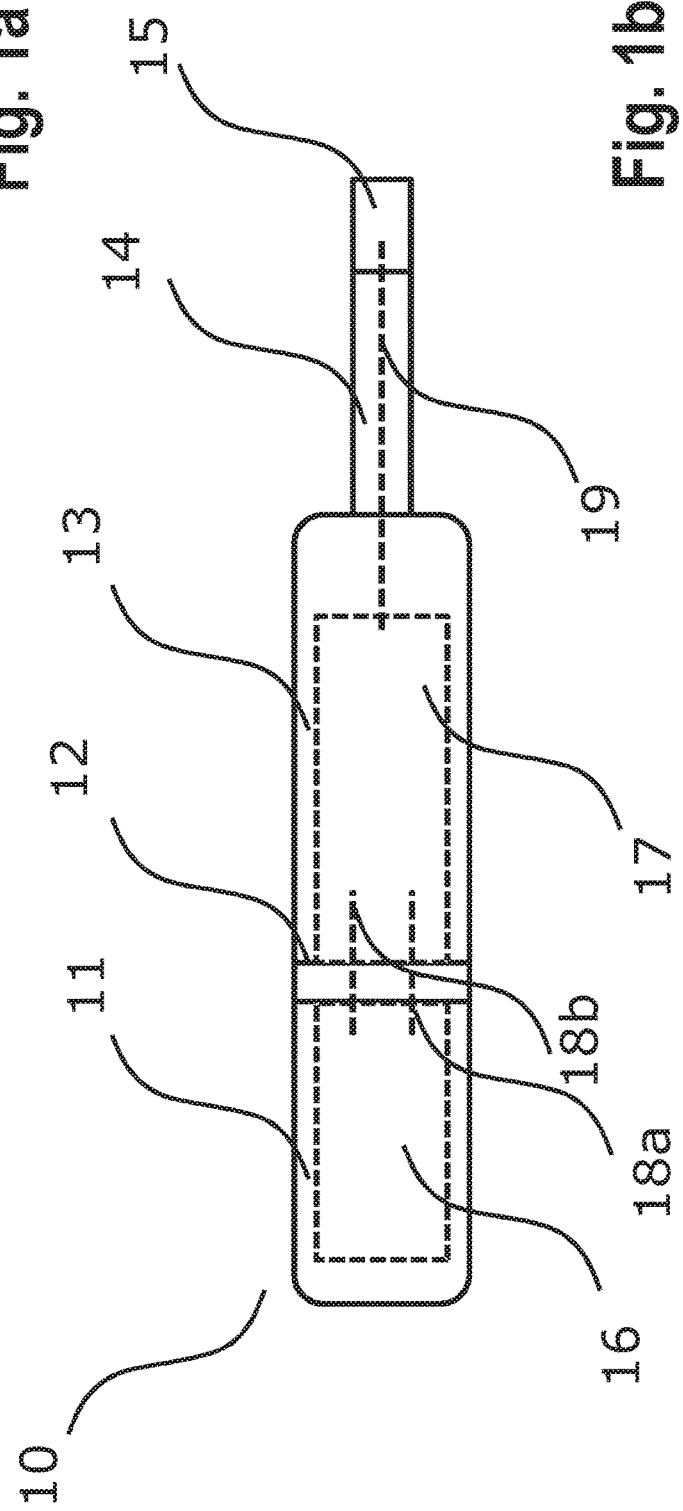

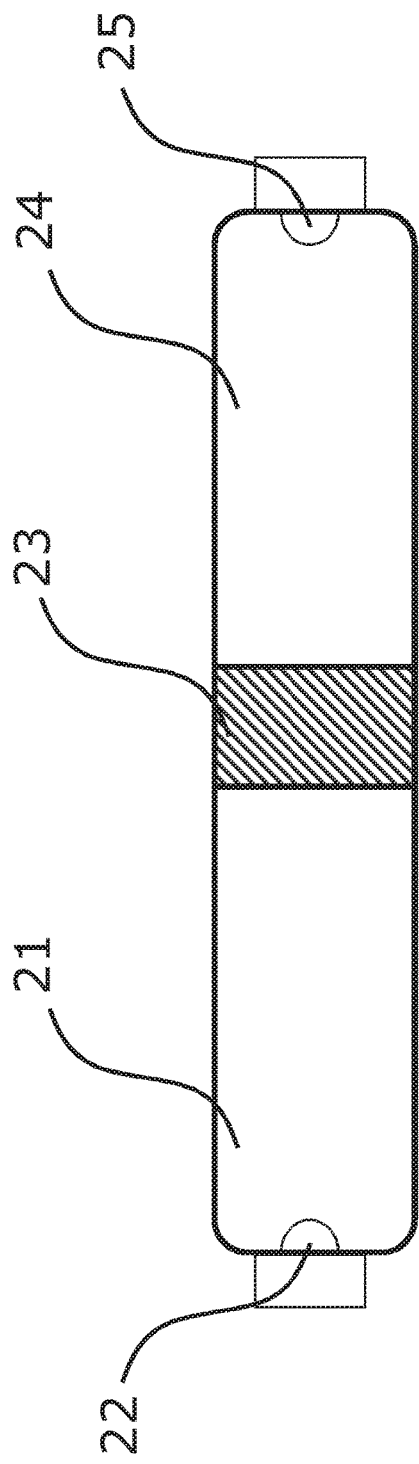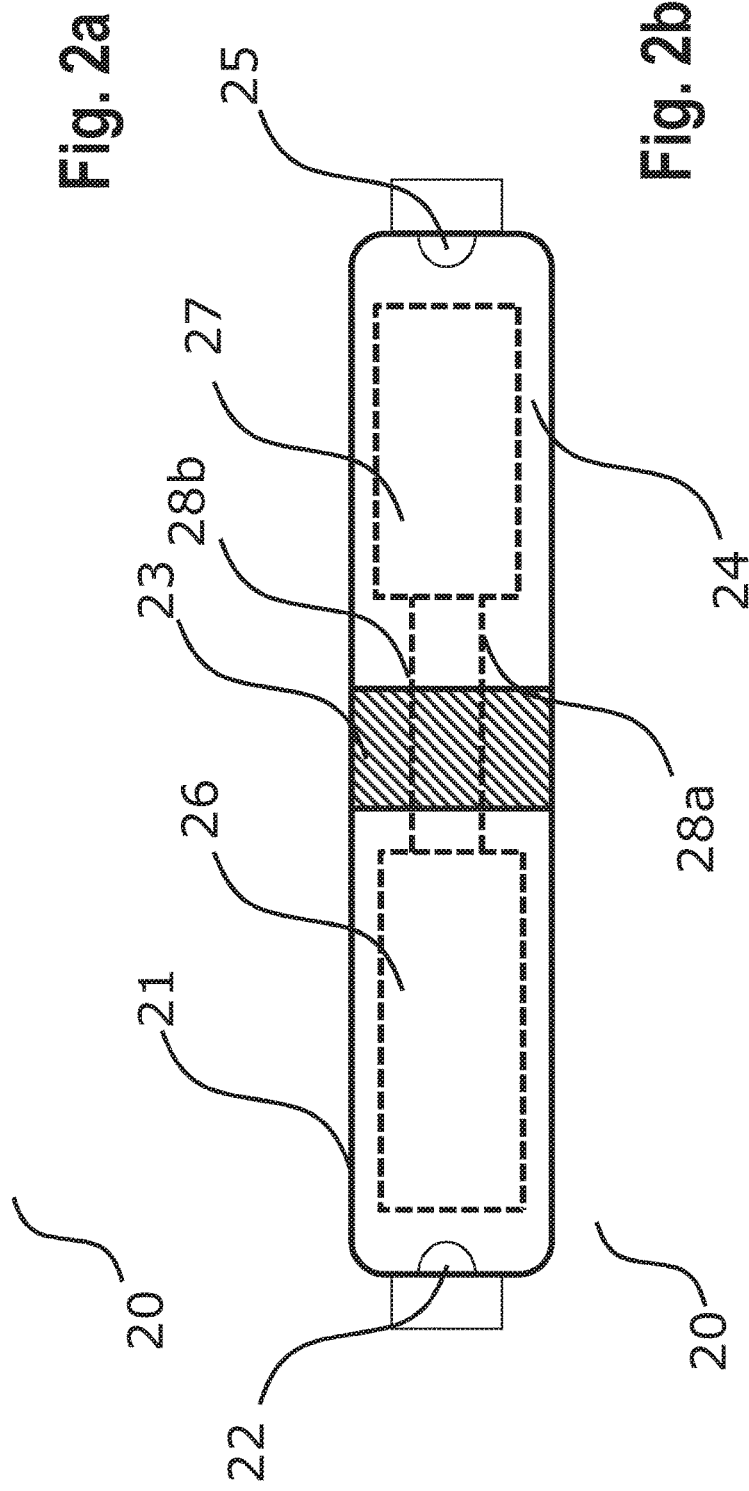

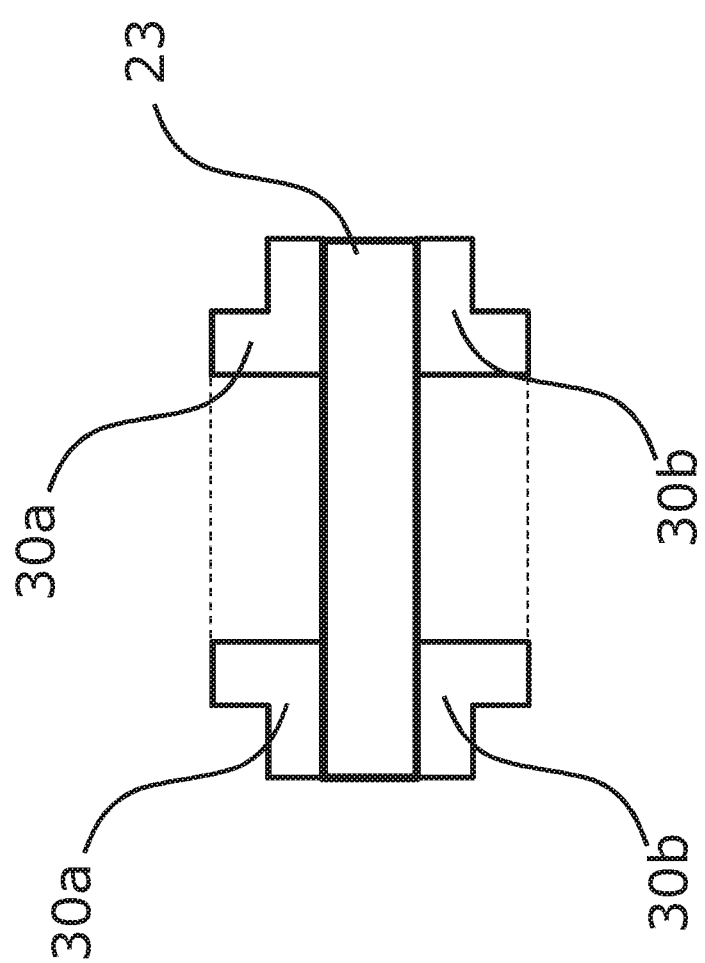

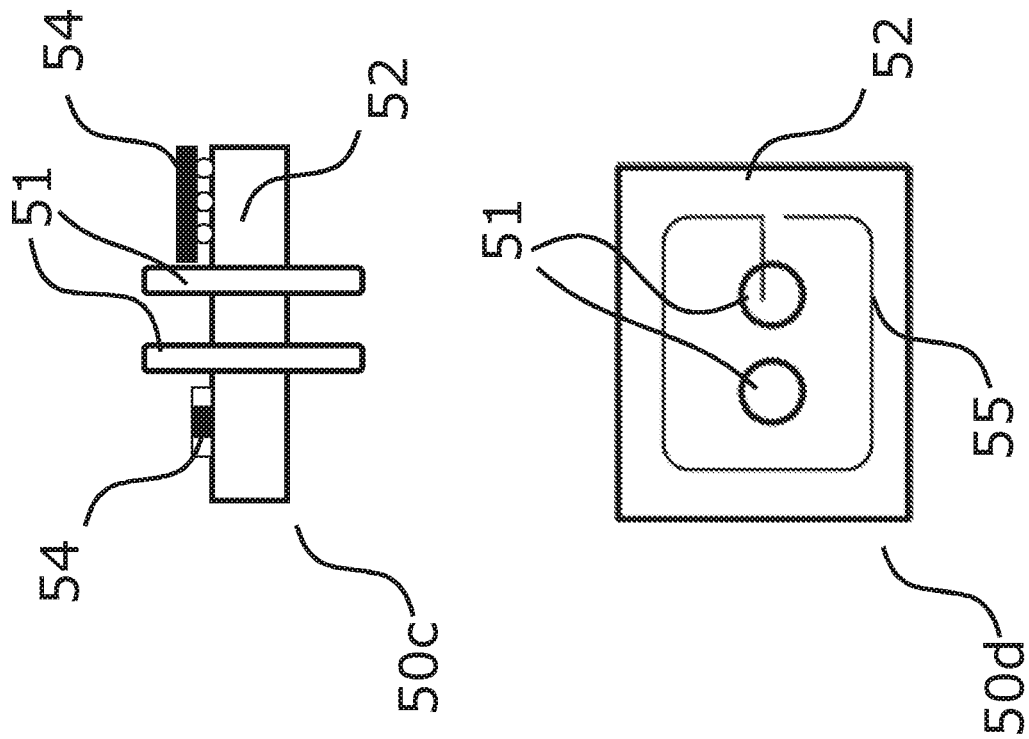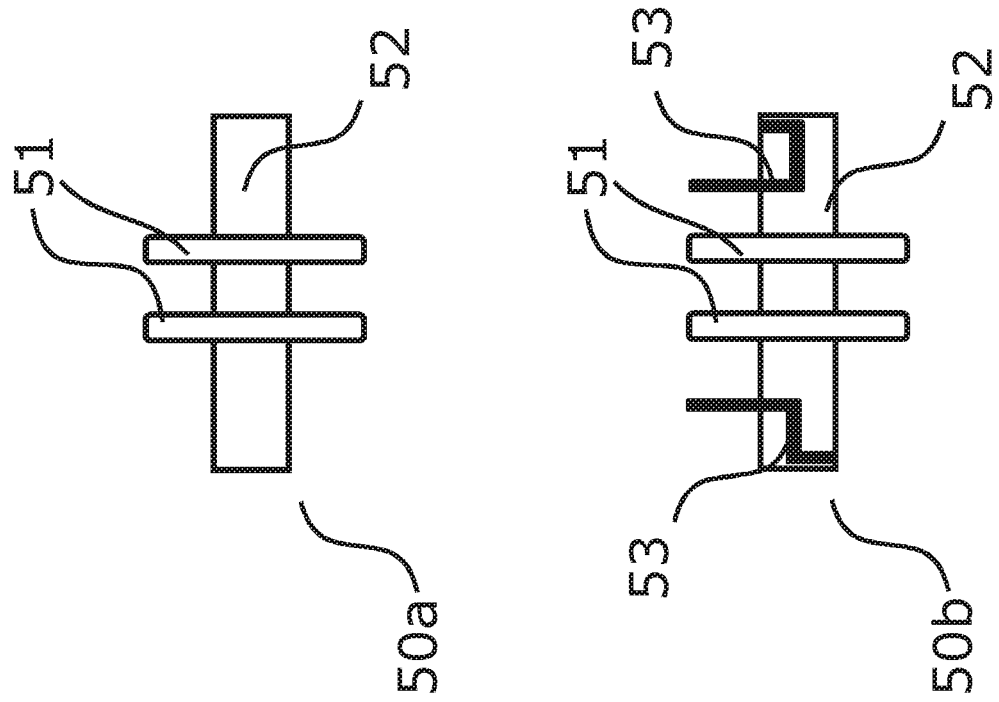
Fig. 5

ELECTROMEDICAL IMPLANT COMPRISING AN ELECTRICAL FEEDTHROUGH

This nonprovisional application claims priority under 35 U.S.C. § 119(a) to German Patent Application No. 10 2016 114 155.0, which was filed in Germany on Aug. 1, 2016, and which is herein incorporated by reference.

BACKGROUND OF THE INVENTION

Field of the Invention

The invention is directed to electromedical implants for measuring, and for delivering electric pulses, or, for example, as an implantable central unit for wireless signal transmission between multiple implants, and to the optimized composition of such implants.

Description of the Background Art

Electromedical implants for measuring electrical potentials and for delivering electric pulses have been used for decades in human and animal bodies for measuring electrical potentials caused by neural activity. Implants used to electrically stimulate neural structures have also been known for quite some time. Disrupted and/or inadequate intrinsic (the body's own) neural activity or stimulus conduction is a typical indication of the need for such an implant. Various measuring and/or stimulation devices exist, which differ in terms of the shape and design, depending on the technical properties and the area of application of the nervous system.

Systems for spinal cord stimulation are used, for example, when neural structures for the functionality of the extremities were damaged and are then used, in general, for pain therapy or to support rehabilitation. Such implants are composed of a device assembly and different electrode leads, for example. The device assembly comprises the device electronics, which include electric circuit arrangements, for example, for measuring and analyzing the electrical potentials and for controlling the electrical stimulation. The device assembly typically also comprises an energy source for the implant, such as a battery, and electrical terminals for the electrode lead. Known electrode leads for such purposes have an elongated lead body, one or more electrodes at the distal end of the lead, and an electrical contact at the proximal end of the lead, by way of which they can be connected to the electrical terminals of the device assembly. During the implantation process, the device assembly is subcutaneously introduced beneath the patient's skin in a suitable location, while the electrode leads are implanted in locations suitable for measuring and stimulating the nerve tissue and are connected to the device assembly.

Known systems for stimulating the heart have a similar composition as the described spinal cord stimulation system. Common cardiac pacemaker systems, implantable cardiac defibrillators or systems used for cardiac resynchronization (cardiac rhythm therapy (CRT) systems) are also typically composed of a device assembly and electrode leads. To measure and stimulate the right half of the heart, electrode leads are advanced via the superior vena cava into the right atrium and right ventricle of the heart and anchored at the desired implantation site. Electrode leads for measuring and stimulating the left half of the heart are typically positioned in a branch of the coronary sinus. The device assembly of such a cardiac stimulator is subcutaneously embedded in the patient's collarbone region and connected to the electrode lead.

Cardiac pacemaker systems that are not equipped with above-described electrode leads are known in the prior art. Such cardiac pacemaker systems are also referred to as 'leadless' systems, or more precisely 'leadless pacemakers.' Such systems comprise a device assembly in which the electrodes for measuring and stimulation are localized on the housing. The device assembly is implanted directly in the atrium or in the ventricle of the heart by way of a catheter system and fixed there.

Furthermore, implantable pure monitoring devices for the heart are known. These are positioned subcutaneously and do not comprise electrode leads that are implanted intracardially. Such devices comprise measuring electrodes on the device housing, which are used to pick up electrical potentials, for example so as to filter out heart signals.

More precisely, known compositions of the aforementioned leadless systems and pure monitoring devices are such that these have a device housing in which the housing electronics and energy supply system are accommodated. Within the housing, the housing electronics and energy supply system are electrically connected to one another via an electrical feedthrough. Furthermore, such a typical composition provides for the device electronics to be connected to a measuring electrode via a further electrical feedthrough. The housing is electrically coupled to the second electrode pole for electrical measurement and/or electrical stimulation and is thus used as a counter pole to the measuring electrode.

An implantable medical device is proposed in US 2015/0073507 A1, for example, wherein the medical device comprises at least two electrodes which are coupled to the device housing.

The previously known leadless systems, implantable monitoring devices and general implantable electromedical devices, and in particular the latter without electrode leads, have a relative complex device composition, such as comprising electrical feedthroughs and separate antennas.

For the described leadless systems, implantable monitoring devices and, in general, for implantable electromedical devices, and in particular the latter without electrode leads, it is advantageous to miniaturize the device composition or device housing.

SUMMARY OF THE INVENTION

It is therefore an object of the present invention to provide a novel implantable electromedical device that has smaller dimensions and a smaller volume than existing known implantable devices of a comparable kind.

It is a further object of the present invention to provide a novel implantable electromedical device that has a novel device composition, which is easy and cost-effective to produce.

According to an exemplary embodiment of the present invention, an electromedical implant is proposed which comprises a housing, wherein the housing comprises three housing segments A, B and C. Housing segment A is joined to housing segment B, and housing segment B is joined to housing segment C, so that housing segment B is disposed between housing segments A and C. Housing segment A and housing segment C are at least partially made of electrically conducting material. Furthermore, the electromedical implant according to an embodiment of the invention comprises an electronics module, which is disposed within housing segment A and comprises an electric circuit arrangement for picking up and further processing electrical signals, and at least one first and one second electrical conductor for measuring electrical potentials and/or for delivering electric pulses, wherein each conductor has a conductor start and a conductor end, and each conductor start is connected to the electric circuit arrangement. The electromedical implant according to the invention also comprises a battery module, which is disposed in the interior of housing segment C, or wherein the battery module comprises a battery housing, which is formed by housing segment C. The electromedical implant according to the invention comprises an electrical feedthrough, wherein the electrical feedthrough is at least partially made of electrically insulating material, and housing segment B is formed by portions of the feedthrough. According to the invention, the electronics module and the battery module are electrically connected via the feedthrough, wherein housing segment A and housing segment C are electrically insulated from one another by the feedthrough. Furthermore, the conductor end of the first electrical conductor is electrically connected via the feedthrough to the portion of housing segment C which is made of electrically conducting material, and the conductor end of the second electrical conductor is electrically connected to the portion of housing segment A which is made of electrically conducting material.

In an embodiment, the electromedical implant according to the invention comprises a single electrical feedthrough.

In the present connection, a "housing segment" can be understood to mean that this involves a section of the housing. Housing segments A and/or C can be made of a single material, such as metal or another electrically conducting material that a person skilled in the art deems useful, which preferably is biocompatible. Furthermore, it is also conceivable that such a segment comprises different materials, such as a material combination or a composite material. Possible suitable materials are biocompatible and conducting metals and metal alloys such as titanium, titanium alloys, stainless steels (such as 316L), other alloys such as MP35N, conducting and biocompatible plastic materials, and plastic or ceramic composite materials. Housing segment B is preferably at least partially made of electrically insulating material. For example, glass, ceramic material, plastic materials or composite materials from among those mentioned above would be suitable for this purpose.

In an embodiment of the electromedical implant according to the invention, housing segment B is made of electrically insulating material, wherein the housing is designed in such a way that housing segment A and housing segment C are electrically insulated from one another by housing segment B.

In an embodiment of the electromedical implant according to the invention, housing segments A and C are configured as housing shells. In the present context, a "housing shell" can be understood to mean a geometric hollow body having at least one opening, which advantageously can be used as part of a housing for an implant according to the present invention. Shapes of the housing shell that, after implantation, ensure high patient comfort and shapes that are accompanied by a low risk of infection after implantation and/or those that are easy to implant and, after implantation, are permanently secured at the implantation site, without shifting or rotating, can be considered advantageous. It is an obvious choice if the shape of the housing shell has a small overall outside surface relative to the inside volume. Additionally, shapes having few corners and edges, or having rounded corners and edges, are an obvious choice. For example, a housing shell can be designed as a hollow cuboid having an open side wall or as a paraboloid.

The electronics module of the electromedical implant according to an embodiment of the invention is disposed in the interior of housing segment A and comprises an electric circuit arrangement. This circuit arrangement comprises, for example, electric circuits for picking up and processing electrical potentials, and units for storing, further signal processing, and signal analysis. Furthermore, the circuit can comprise components for delivering electric pulses and for coordinating these pulses. Circuit components for wireless data transmission (telemetry) of measured and stored data to external systems or an external patient device would likewise be conceivable. The electronics module furthermore comprises at least one first and second conductor. The conductors are connected with the respective conductor start thereof to the electric circuit arrangement.

In the context of the present invention, an "electrical conductor" can, in general, be understood to mean an electrical conductor connection with which the electronic elements can make contact. Such a conductor connection can be designed, for example, as a conductor wire having a conductor start and a conductor end, or as a conductive track on a printed circuit board having an electrical contacting option at the start and end of the conductive track, or as a conducting portion of an electrical feedthrough, or a combination of these options and further options a person skilled in the art deems useful.

The battery module is disposed in the interior of housing segment C. In an embodiment, there is no direct electrical connection between the battery module and housing segment C. The expression "no direct electrical connection" within the meaning of the embodiment of the invention can be understood to mean that the battery module and housing segment C are to be electrically insulated in such a way that no direct electrical connection is implemented between the battery module and housing segment C via an electrical conductor. The reason behind this is that, in a preferred embodiment of the invention, housing segment C is electrically connected to the electric circuit arrangement of the electronics module, and that the electrical potential of the portion of housing segment C made of electrically conducting material is determined by this connection.

According to an embodiment of the present invention, the electromedical implant according to the invention comprises an electrical feedthrough. Within the meaning of the invention, an electrical feedthrough can be understood to mean an element for electrical conduction, which is designed to transfer or couple an electrical signal from one environment into another, wherein signal properties and quality are to be preserved to as great an extent as possible. For example, this may be the coupling of a signal into a device housing, or from one housing segment into another housing segment. Within the meaning of the invention, the electrical feedthrough comprises a feedthrough body, in which the electrical conductor elements are integrated or through which electrical conductor elements pass. The conductor elements in each case lead from a first outer surface of the feedthrough body through the feedthrough body to a second outer surface of the feedthrough body. The first and second outer surfaces can represent the same outer surface or different outer surfaces of the feedthrough body. The conductor elements comprise electrical contacts at the ends, which protrude beyond the corresponding outer surface and via which the electrical signal can be coupled into the feedthrough. In one embodiment, the aforementioned electrical contacts can be attached to the feedthrough body by way of soldering. The feedthrough body is preferably at least partially made of an electrically insulating material. In one embodiment, the entire feedthrough body is made of such a material. In any case, however, within the meaning of the invention the electrical feedthrough or the feedthrough body is configured to electrically insulate housing segments A and C from one another, so that no direct current path exists from housing segment A via the feedthrough to housing segment C. Housing segment B is formed by portions of the feedthrough, for example by a number of outer surfaces of the feedthrough body. For example, the totality of housing segment B can be formed by portions of the feedthrough or of the feedthrough body. Within the housing, as mentioned above, the electronics module is disposed in the interior of housing segment A, while the battery module is disposed in the interior of housing segment C. The electronics module and the battery module are preferably electrically connected to one another via/through of the feedthrough. This can be ensured by additional electrical conductors, which connect the electronics module to electrical contacts on the side of the feedthrough directed toward the electronics module, and by additional electrical conductors, which connect the battery module to electrical contacts on the side of the feedthrough directed toward the battery module.

Furthermore, the aforementioned first electrical conductor, the conductor start of which is connected to the electric circuit arrangement, is connected at the conductor end to a portion of housing segment C, which is made of electrically conducting material, wherein the first conductor passes through the feedthrough. The current path of the first conductor thus leads from the electric circuit arrangement through the feedthrough to housing segment C, which is made of electrically conducting material. The aforementioned second electrical conductor, the conductor start of which is likewise connected to the electric circuit arrangement, is connected at the conductor end to the portion of housing segment A made of electrically conducting material. According to the present invention, no further electrical connection exists between housing segment A or C and the electronics module or the battery module, except for the electrical connections via the first and second conductors (and potentially necessary ground potential connections). In this way, a current path is generated which leads from the electric circuit arrangement of the electronics module to the electrically conducting portion of housing segment A, from there to the electrically conducting portion of housing segment C, and then via the second conductor through the feedthrough back to the electric circuit arrangement. Consequently, the two electrode poles needed for measuring and/or delivering electric pulses are formed by the electrically conducting portions of housing segment A and housing segment C. As mentioned above, housing segment(s) A and/or C can also be made entirely of electrically conducting material.

In an embodiment of the present invention, contact is optionally made with housing segments A and C by way of further electrical conductors passing through the feedthrough. In one embodiment, it is conceivable that housing segment A or C (or the electrically conducting portion of the respective segment) is fixed to the positive or negative pole of the battery of the battery module. It is also conceivable that the electrical potential of the electrically conducting portions of housing segments A and C is designed to be floating.

In an embodiment of the electromedical implant according to the invention, the housing of the implant has an elongated shape, wherein housing segments A and C are configured as housing shells. The housing shells are each fixedly joined to the feedthrough at the open ends. This is preferably a soldered or welded joint.

According to an embodiment, the electromedical implant according to the invention can be, for example, a cardiac implant in the form of a sensor, a monitoring device, a pacemaker device, a pacemaker device having an integrated defibrillator function or a pacemaker device without intracardiac electrodes. All implantable electromedical devices that comprise two electrodes and are advantageous for a miniaturization of the implant would also be conceivable. In a preferred embodiment of the invention, the electromedical implant is purely a cardiac monitoring implant or a miniaturized cardiac pacemaker implant without intracardiac electrode leads, or a leadless pacemaker implant.

According to an embodiment, the electromedical implant according to the invention can be a neurostimulation implant in the form of a spinal cord stimulation device, a vagus nerve stimulation device, or a brain stimulation device. A design of the electromedical implant as a muscle stimulation device would also be conceivable.

In an embodiment of the invention, housing segment A and/or housing segment C of the proposed electromedical implant comprise a coating made of electrically insulating material, wherein housing segment A and/or housing segment C comprise at least one region having no coating made of electrically insulating material. The region preferably does not abut housing segment B. In an embodiment of the electromedical implant according to the invention, housing segment A and/or housing segment C at least partially comprise a coating that improves electrical coupling, such as a fractal coating having surface-enlarging properties, and/or the coating has bioactive properties.

Advantageous materials for such a coating are, for example, silicones, Parylene, diamond-like carbon (DLC) paints, powder coatings or nanocoatings, or a mixture or a combination of the aforementioned materials.

Such a coating can be used to determine the electrical path from housing segment A to C via the tissue (this path represents the electrical measurement and/or stimulation vector). For this purpose, the areas in which the current is to enter or exit the housing segment are not coated. Preferably, the current path for the measurement and/or stimulation vector is selected so as to be sufficiently long. When the electromedical implant according to the invention has an elongated shape, the aforementioned exit areas are preferably designed in such a way that these are located at the ends of the longitudinal axis of the implant.

According to an embodiment of the electromedical implant according to the invention, the electrical feedthrough, or the feedthrough body of the electrical feedthrough, is made of a ceramic material and/or a composite material. Suitable materials, by way of example, are Al2O3, ZrO2, Ti2O. Multilayer technology materials are likewise conceivable materials for the described purpose, such as multilayer technology ceramic materials (high-temperature co-fired ceramics (HTCC), low-temperature co-fired ceramics (LTCC)).

In an embodiment of the present invention, the electromedical implant comprises at least one active or passive component, wherein the component is integrated in the feedthrough and/or joined to the feedthrough.

Passive or active electronic components, by way of example, are passive or active filters, and passive or active assemblies for radio frequency (RF) applications, such as for signal transmission using external devices, or signal transmission within a combination of active implants and/or passive or active assemblies for managing the battery.

According to an embodiment, the electromedical implant according to the invention comprises an antenna, which is integrated in the feedthrough and/or joined to the feedthrough. The antenna is used to send and receive data to/from an external system or an external device for the purpose of telemetry. All antenna types and shapes that can be considered useful by a person skilled in the art and that can be integrated on or in the feedthrough are conceivable here.

In an embodiment, the electromedical implant according to the invention comprises an antenna formed by the two housing segments A and C of the electromedical implant which are electrically insulated from one another (and the resulting electric dipole).

In an embodiment of the electromedical implant according to the invention, housing segment A is joined to housing segment B and/or housing segment B is joined to housing segment C by way of a low-temperature solder joint, a laser solder joint, a cold weld joint, a friction weld joint, a fusion weld joint, an adhesive joint or an ultrasonic joint.

According to an embodiment of the electromedical implant according to the invention, the electrical feedthrough has a composition comprising multiple layers, wherein the layers are alternately made of electrically insulating material and electrically conducting material. When using such a feedthrough, it is conceivable in a further embodiment to position further electrode poles for measurement and/or stimulation on the outer surfaces of the layers made of electrically conducting material, whereby multipolar measurements and/or stimulations can be carried out. It is also possible to implement passive or active electronic components within the composition comprising multiple layers.

Furthermore, a method for producing an electromedical implant is provided, comprising: providing an electronics module, comprising an electric circuit arrangement for picking up and further processing electrical signals, having at least two electrical conductors for measuring electrical potentials; providing a battery module, an electrical feedthrough, wherein the feedthrough is at least partially made of electrically insulating material, a housing shell A and a housing shell C, wherein housing shells A and C are at least partially made of electrically conducting material; disposing the feedthrough between the electronics module and the battery module; establishing an electrical connection between the electronics module and the battery module via the feedthrough; establishing an electrical connection between the electric circuit arrangement and the portion of housing shell A made of electrically conducting material; establishing an electrical connection between the electric circuit arrangement and the portion of housing shell C made of electrically conducting material via the feedthrough; attaching housing shell A on the side of the feedthrough located toward the electronics module so that the electronics module is disposed within housing shell A and is hermetically sealed; and attaching housing shell C on the side of the feedthrough located toward the battery module so that the battery module is disposed within housing shell C and is hermetically sealed so that housing shell A and housing shell C are electrically insulated from one another by the feedthrough.

In the present context, a "housing shell" can be understood to mean a geometric hollow body having at least one opening, which advantageously can be used as part of a housing for an implant according to the present invention. Shapes of the housing shell that, after implantation, ensure high patient comfort and shapes that are accompanied by a low risk of infection after implantation and/or those that are easy to implant and, after implantation, are permanently secured at the implantation site, without shifting or rotating, can be considered advantageous. It is an obvious choice if the shape of the housing shell has a small overall outside surface relative to the inside volume. Additionally, shapes having few corners and edges, or having rounded corners and edges, are an obvious choice. For example, a housing shell can be designed as a hollow cuboid having an open side wall or as a paraboloid. Housing shells A and/or C can be made of a single material, such as metal or another electrically conducting material that a person skilled in the art deems useful, which preferably is biocompatible. Furthermore, it is also conceivable that a housing shell comprises different materials, such as a material combination. Possible suitable materials are, for example, metal/plastic composites, metal/ceramic composites, and metal/glass composites. The electrical feedthrough comprises a feedthrough body, which is preferably at least partially made of electrically insulating material. For example, glass, ceramic material, plastic materials or composite materials from among those mentioned above would be suitable for this purpose.

The electronics module can be disposed in the interior of housing shell A and comprises an electric circuit arrangement. This circuit arrangement comprises, for example, electric circuits for picking up and processing electrical potentials, and units for storing, further signal processing, and signal analysis. Furthermore, the circuit can comprise components for delivering electric pulses and for coordinating these pulses. Circuit components for wireless data transmission (telemetry) of measured and stored data to external systems or an external patient device would likewise be conceivable. The electronics module furthermore comprises at least one first and second conductor. The conductors are connected with the respective conductor start thereof to the electric circuit arrangement.

In connection with the method according to the invention, "establishing an electrical connection" can, in general, be understood to mean the implementation of an electrical conductor connection so that contact is made with electronic elements. Such a conductor connection can be designed, for example, as a conductor wire having a conductor start and a conductor end, or as a conductive track on a printed circuit board having an electrical contacting option at the start and end of the conductive track, or as a conducting portion of an electrical feedthrough, or a combination of these options and further options a person skilled in the art deems useful.

According to the method according to the invention, the battery module is disposed in the interior of housing shell C. In an embodiment, no direct electrical connection exists between the battery module and housing shell C.

In connection with the method according to the invention, an electrical feedthrough is provided for the electromedical implant. Within the meaning of the invention, an electrical feedthrough can be understood to mean an element for electrical conduction, which is designed to transfer or couple an electrical signal from one environment into another, wherein signal properties and quality are to be preserved to as great an extent as possible. For example, this may be the coupling of a signal into a device housing, or from one housing section into another housing section. Within the meaning of the invention, the electrical feedthrough comprises a feedthrough body, in which the electrical conductor elements are integrated or through which electrical conductor elements pass. The conductor elements in each case lead from a first outer surface of the feedthrough body through the feedthrough body to a second outer surface of the feedthrough body. The first and second outer surfaces can represent the same outer surface or different outer surfaces of the feedthrough body. The conductor elements comprise electrical contacts at the ends, which protrude beyond the corresponding outer surface and via which the electrical signal can be coupled into the feedthrough. In one embodiment, the aforementioned electrical contacts can be attached to the feedthrough body by way of soldering. The feedthrough body is preferably at least partially made of an electrically insulating material. In one embodiment, the entire feedthrough body is made of such a material. In any case, however, within the meaning of the method according to the invention, the electrical feedthrough or the feedthrough body is configured to electrically insulate housing shells A and C from one another, so that no direct current path exists from housing shell A via the feedthrough to housing shell C. Within the housing, as mentioned above, the electronics module is disposed in the interior of housing shell A, while the battery module is disposed in the interior of housing shell C. The electronics module and the battery module are preferably electrically connected to one another via/through of the feedthrough. This can be ensured by additional electrical conductors, which connect the electronics module to electrical contacts on the side of the feedthrough directed toward the electronics module, and by additional electrical conductors, which connect the battery module to electrical contacts on the side of the feedthrough directed toward the battery module.

Within the meaning of the method according to the invention, the feedthrough is disposed between the electronics module and the battery module. The electronics module is electrically connected to the battery module via the electrical lines in the feedthrough; furthermore, electrical connections are established between the electric circuit arrangement and the portion of housing shell A made of electrically conducting material, and between the electric circuit arrangement and the portion of housing shell C made of electrically conducting material via the feedthrough. Housing shells A and C are each attached on the side of the feedthrough located toward the electronics module or toward the battery module. Within the meaning of the invention, "attaching" can be understood to mean a joining of the corresponding components, so that a stable, secure material bond is created, for example by way of soldering, welding or gluing. According to the proposed method, housing shells A and C are thus electrically insulated from one another by the feedthrough. According to the proposed method, a current path is generated between housing shell A or C and the electronics module or the battery module, the current path leading from the electric circuit arrangement of the electronics module to the electrically conducting portion of housing shell A, from there to the electrically conducting portion of housing shell C, and then through the feedthrough back to the electric circuit arrangement. Consequently, the two electrode poles needed for measuring and/or delivering electrical pulses are formed by the electrically conducting portions of housing shell A and housing shell C. As mentioned above, housing shell(s) A and/or C can also be made entirely of electrically conducting material.

In an embodiment of the method according to the invention, the method comprises the step of making contact with housing shells A and C by way of further electrical conductors passing through the feedthrough. In an embodiment, it is conceivable that housing shells A and C (or the electrically conducting portion of the respective housing shell) is fixed to the positive or negative pole of the battery of the battery module. It is also conceivable that the electrical potential of the electrically conducting portions of housing shells A and C is designed to be floating.

In an embodiment of the method according to the invention, the electromedical implant is designed as a cardiac implant in the form of a sensor, a monitoring device, a pacemaker device, a pacemaker device having an integrated defibrillator function or a pacemaker device without intracardiac electrodes.

According to an embodiment, the method according to the invention for producing an electromedical implant comprises at least the further step of coating housing shell A and/or housing shell C with electrically insulating material, wherein a region of housing shell A and/or housing shell C is not coated, wherein the region does not abut the feedthrough.

Advantageous materials for such a coating are, for example, silicones, Parylene, diamond-like carbon (DLC) paints, powder coatings or nanocoatings, or a mixture or a combination of the aforementioned materials.

Such a coating can be used to determine the electrical path from housing shell A to C via the tissue (this path represents the electrical measurement and/or stimulation vector). For this purpose, the areas in which the current is to enter or exit the housing shell are not coated. Preferably, the current path for the measurement and/or stimulation vector is selected so as to be sufficiently long. When the electromedical implant according to the invention has an elongated shape, the aforementioned exit areas are preferably designed in such a way that these are located at the ends of the longitudinal axis of the implant.

In an embodiment for the method according to the invention for producing an electromedical implant, the attaching of housing shell A and/or housing shell B takes place by way of low-temperature soldering, laser soldering, cold welding, friction welding, fusion welding, gluing or ultrasonic welding.

According to an embodiment, the method according to the invention for producing an electromedical implant comprises at least the further step of integrating at least one passive or active component and/or an antenna in the feedthrough. The antenna is used to send and receive data to/from an external system or an external device for the purpose of telemetry. All antenna types and shapes that can be considered useful by a person skilled in the art and that can be integrated on or in the feedthrough are conceivable here.

In an embodiment of the method according to the invention, the electrical feedthrough has a composition comprising multiple layers, wherein the layers are alternately made of electrically insulating material and electrically conducting material. When using such a feedthrough, it is conceivable in a further embodiment to position further electrode poles for measurement and/or stimulation on the outer surfaces of the layers made of electrically conducting material, whereby multipolar measurements and/or stimulations can be carried out. It is also possible to implement passive or active electronic components within the composition comprising multiple layers.

In an embodiment of the method according to the invention for producing an electromedical implant, housing shell A and/or housing shell C are composed of two joined half shells. Such a modular composition of the housing shells allows a simplified manufacture of the housing shells. For example, the half shells can be joined to form a housing shell by welding.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1a shows an outer composition of an exemplary implantable device for measuring electrical potentials from the related art;

FIG. 1b shows outer and inner compositions of an exemplary implantable device for measuring electrical potentials from the related art;

FIG. 2a shows an outer composition of an exemplary electromedical implant according to the invention;

FIG. 2b shows outer and inner compositions of an exemplary electromedical implant according to the invention;

FIG. 3 shows a preferred attachment between the electrical feedthrough and the abutting housing segments according to the invention;

FIG. 5 shows exemplary embodiments of the electrical feedthrough of the electromedical implant according to the invention;

DETAILED DESCRIPTION

Figure 4:
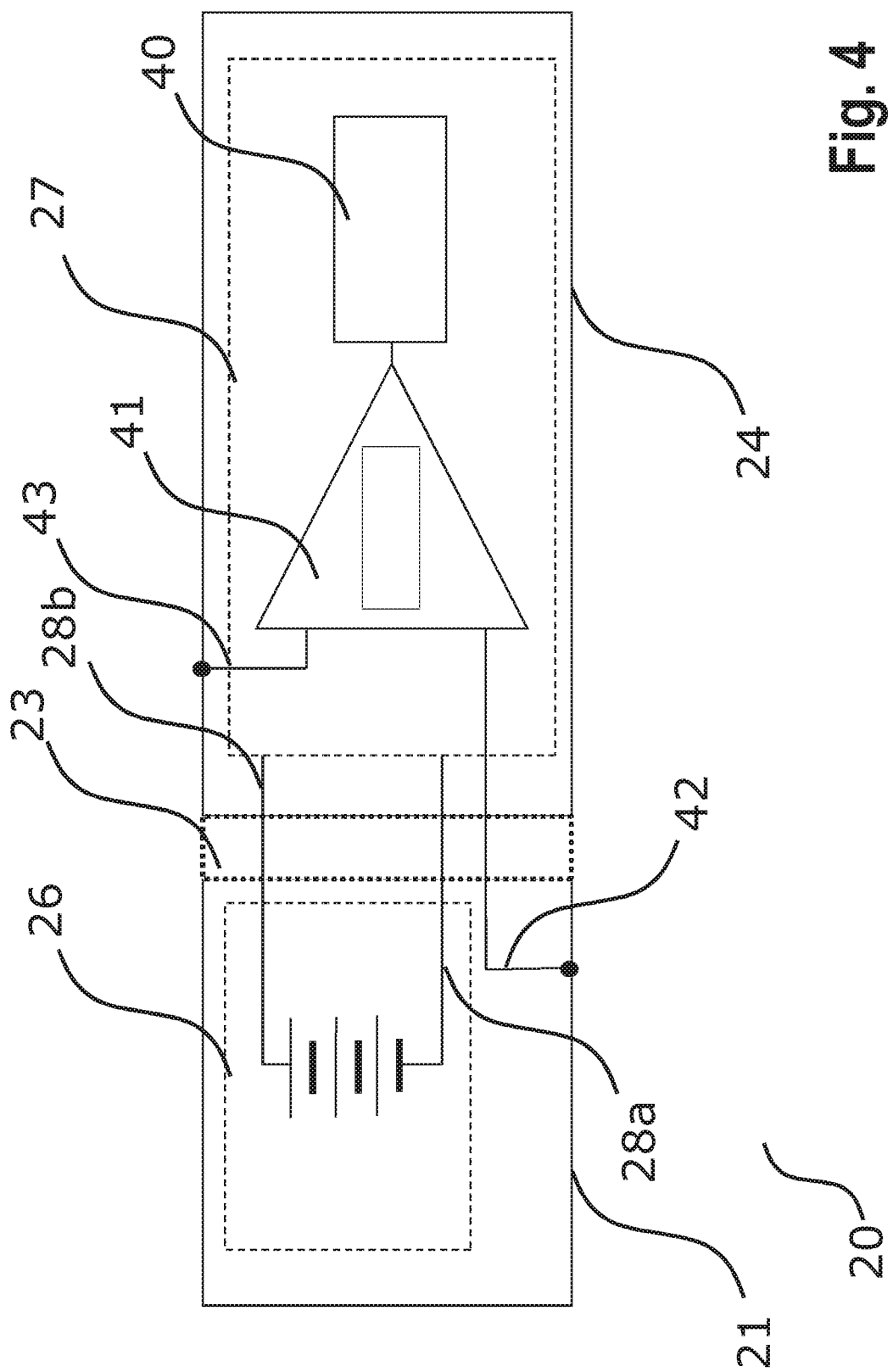
FIG. 4 shows an advantageous embodiment of the electrical connection and interconnection for the electromedical implant according to the invention.

FIGS. 1a and 1b show an exemplary implantable device 10 for measuring electrical potentials from the related art. FIG. 1a illustrates the outer composition of such an implanted device 10, comprising a housing including a battery housing 11, a battery cover having a first feedthrough 12, and an electronics housing 13. The implantable device 10 furthermore comprises a second feedthrough 14 and a measuring electrode 15. FIG. 1b, in dotted lines, shows the inner composition of the implantable device 10, comprising a battery module 16, an electronics module 17, electrical connections 18a and 18b, which electrically connect the battery module 16 and the electronics module 17 via the feedthrough in the battery cover 12, and an electrical connection 19, which connects the electronics module to the measuring electrode 15. The counter-electrode to the measuring electrode 15 can be formed by the housing.

FIGS. 2a and 2b show an exemplary embodiment of an electromedical implant 20 within the meaning of the invention. FIG. 2a illustrates the outer composition of the electromedical implant 20, comprising a first housing segment 21 having a portion 22 made of electrically conducting material, an electrical feedthrough 23, and a second housing segment 24 having a portion 25 made of electrically conducting material. FIG. 2b schematically shows the inner composition (dotted lines) of the exemplary embodiment of FIG. 2a, comprising a battery module 26, an electronics module 27 and two electrical connections 28a and 28b, which electrically connect the battery module 26 and the electronics module 27 via the feedthrough 23. Further electrical connections and interconnections provided for the functionality of the invention are not shown in FIG. 2b for clarity reasons. The portions 22 and 25 of the housing segments 21 and 24 which are made of electrically conducting material represent the electrical poles for measurement and/or stimulation. In the exemplary electromedical implant 20, 22 and 25 are located at the ends of the longitudinal axis of the electromedical implant. This offers the advantage of a relatively long measurement or stimulation vector so as to be able to carry out measurements having high informational content, which is to say to obtain more representative measurements. As an alternative, housing segments 21 and 24 can also be made completely of electrically conducting material. It is then possible to implement 22 and 25 by providing the housing segments 21 and 24 with an electrically insulating coating, wherein the areas on 22 and 25 are not coated. In the exemplary embodiment of the electromedical implant 20, the housing segments 21 and 24 are configured as elongated half shells, which are joined at the open ends thereof to the feedthrough. In the present example, the interior of the electromedical implant 20 is hermetically sealed by housing segments 21 and 24, in conjunction with the feedthrough 23.

FIG. 3 shows an exemplary embodiment of the attachment between the feedthrough 23 and the abutting housing segments 21 and 24 in a sectional view. For example, initially, metallic terminal contacts can be soldered to the feedthrough 23 so as to then attach the housing segments at the appropriate interfaces 30a and 30b to the feedthrough, for example by way of laser welding.

FIG. 4 shows an exemplary embodiment of the electrical connection and interconnection for the electromedical implant according to the invention. Corresponding to the embodiment of FIGS. 2a and 2b, the electromedical implant 20 comprises a first housing segment 21, an electrical feedthrough 23, and a second housing segment 24. In the interior of the electromedical implant 20, a battery module 26, an electronics module 27 and two electrical connections 28a and 28b are located, which electrically connect the battery module 26 and the electronics module 27 via the feedthrough 23. The electronics module comprises an electric circuit arrangement 40, which can include, for example, electric circuits for picking up and processing electrical potentials, and units for storing, further signal processing and signal analysis. Furthermore, the circuit can comprise components for delivering electric pulses and for coordinating these pulses. Circuit components for wireless data transmission (telemetry) of measured and stored data to external systems or an external patient device would likewise be conceivable. The electronics module 27 furthermore comprises at least one first conductor 42 and one second conductor 43. The conductor 42 is electrically connected to the housing segment 21, or to the portion of the housing segment 21 made of electrically conducting material, and passes through the electrical feedthrough 23 to the electronics module 27. The conductor 42 can lead into the first input of an operational amplifier 41. The conductor 43 is electrically connected to the housing segment 24, or to the portion of the housing segment 24 made of electrically conducting material, and leads to the electronics module 27. The conductor 43 can lead into a second input of the operational amplifier 41. The picked-up electrical potentials via the conductors 42 and 43 are amplified by the amplifier 41 and relayed to the electric circuit arrangement 40, where they are further processed.

FIG. 5 schematically shows exemplary embodiments 50a, 50b and 50c for the electrical feedthrough of the electromedical implant according to the invention in a sectional view. Embodiment 50d shows the electrical feedthrough of the electromedical implant in the view from above. Feedthrough variant 50a comprises a feedthrough body 52 and two electrical contacts 51, which pass through the feedthrough body, at the ends of which electrical contacts can be attached (such as by way of soldering). Feedthrough variant 50b comprises additional electrical tracks 53, which pass through the feedthrough body 52. These additional conductors can be used for further modifications and adjustments of the electrical potentials of the housing segments, such as to configure the electrical potentials to be floating. Feedthrough variant 50c comprises further components 54, which can be integrated on or in the feedthrough body 52 and/or can be joined to the feedthrough body 52. Exemplary components include electronic passive or active components or antenna forms for the purpose of telemetry. Exemplary embodiment 50d shows a variant of the feedthrough in which an antenna 55 is integrated in the feedthrough, so that, for example, the antenna 55 can be incorporated into the feedthrough body 52, or the antenna 55 is joined to the feedthrough, such as applied to the surface of the feedthrough body 52.

Figure 6:
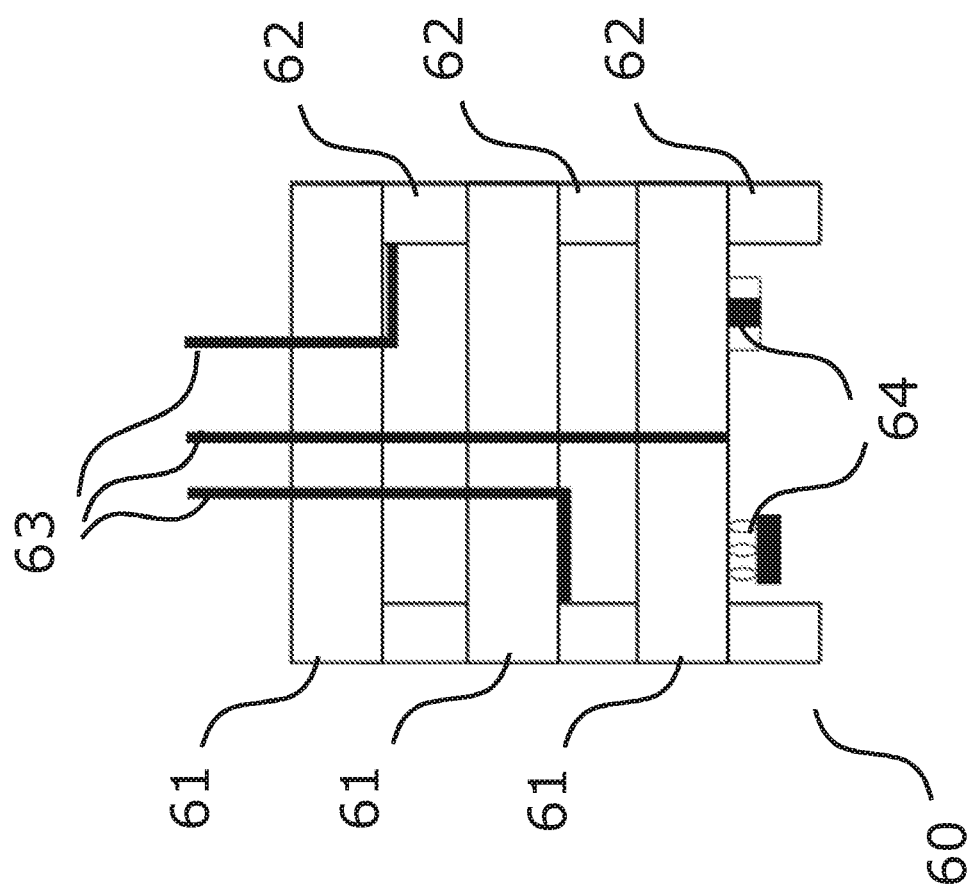
FIG. 6 shows an exemplary embodiment of the electrical feedthrough of the electromedical implant having a multi-layer composition according to the invention.

FIG. 6 schematically shows an exemplary embodiment 60 of the electrical feedthrough of the electromedical implant having a multilayer composition according to the invention in a sectional view. The feedthrough 60 comprises multiple alternating layers made of electrically insulating material 61 and electrically conducting material 62. Electrical conductors 63 pass through the layers and contact can be established therewith in such a way that further electric poles can be created on the layers made of electrically conducting material 62. These poles can be used to measure further electrical potentials or to deliver electric pulses. Furthermore, the feedthrough 60 can comprise additional electronic components 64, which are integrated on and/or in the layers and/or joined to the layers. Exemplary components include electronic passive or active components, or antenna forms for the purpose of telemetry.

Figure 7:
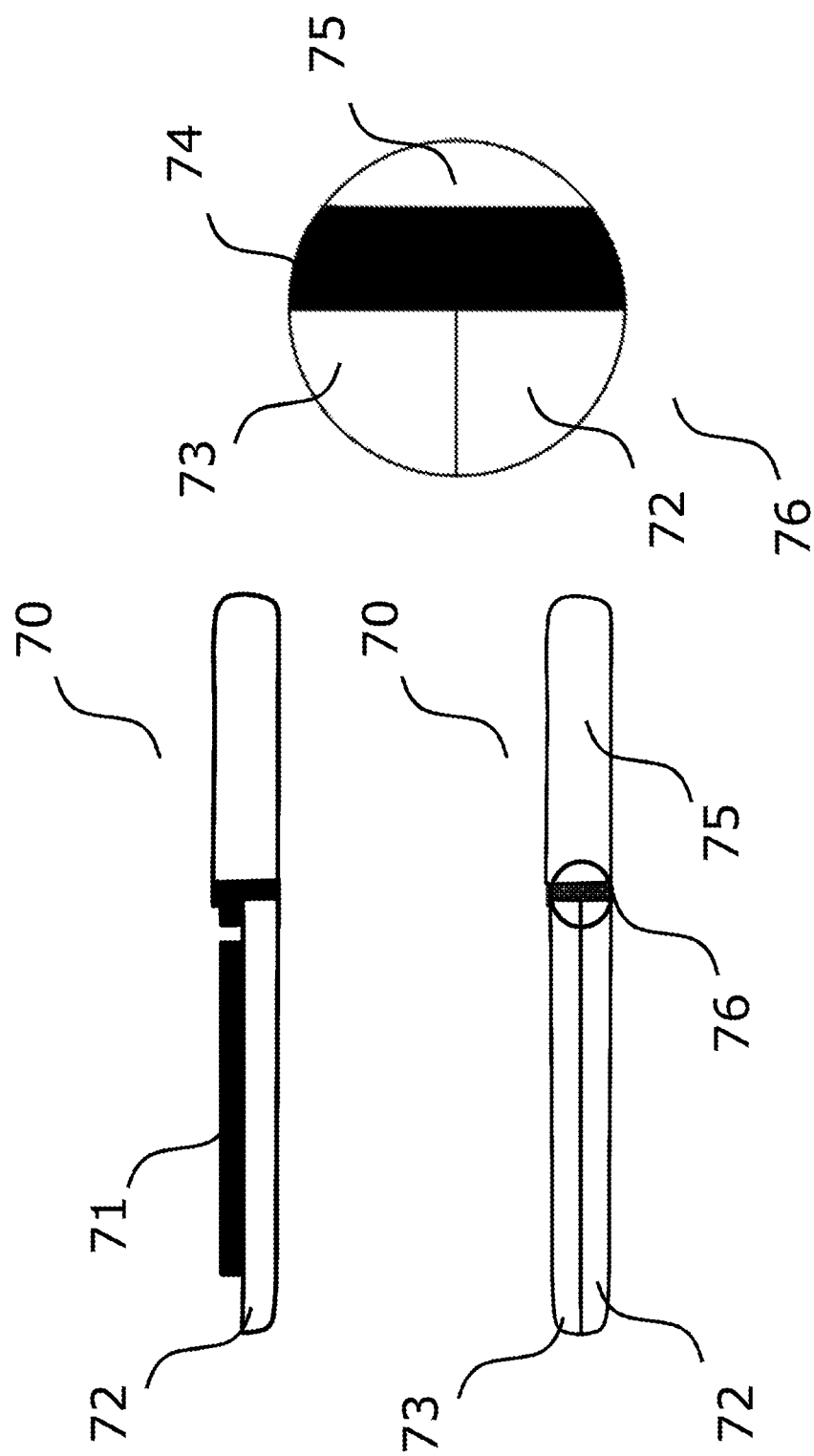
FIG. 7 shows an embodiment of the housing segments as housing shells, which are composed of half shells.

FIG. 7 shows an embodiment of the electromedical implant 70 within the meaning of the invention, in which the housing segments are configured as housing shells, wherein one housing shell is composed of two half shells. FIG. 7 shows side views of the embodiment of the electromedical implant 70, wherein the housing segment accommodating the module 71 is joined from two half shells 72 and 73. The module 71 can represent the battery module or the electronics module according to the invention. Region 76, in detail, shows the area in which the half shells 72 and 73 abut the feedthrough 74. Housing segment 75 is one embodiment of the housing segment according to the invention in the form of a housing shell and can also be composed of two half shells. A composition of a housing segment according to the invention from more than two components would also be conceivable. The joining of the half shells 72 and 73, or the attaching of the half shells 72 and 73 to the feedthrough 74, can take place by way of joining methods, such as low-temperature soldering, laser soldering, cold welding, friction welding, fusion welding, gluing or ultrasonic welding.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. An electromedical implant comprising:
a housing, comprising three housing segments A, B and C, the housing segment A being joined to the housing segment B and the housing segment B being joined to housing segment C so that the housing segment B is disposed between the housing segments A and C, housing segment A and housing segment C being at least partially made of electrically conducting material;
an electronics module arranged within housing segment A, the electronics module comprising an electric circuit arrangement adapted to pick up and further process electrical signals, and at least one first and one second electrical conductor to measure electrical potentials and/or to deliver electric pulses, the first and second conductors having a conductor start and a conductor end, the conductor start of the first and second conductors being connected to the electric circuit arrangement;
a battery module comprising a battery housing formed by the housing segment C; and
a single electrical feedthrough being at least partially made of an electrically conducting material,
wherein the housing segment B is formed by at least portions of the feedthrough,
wherein the electronics module and the battery module are electrically connected via the feedthrough,
wherein the housing segment A and the housing segment C are electrically insulated from one another by the feedthrough, and
wherein the conductor end of the first electrical conductor is electrically connected via the feedthrough to a portion of housing segment C made of the electrically conducting material, and
wherein the conductor end of the second electrical conductor is electrically connected to the portion of housing segment A made of the electrically conducting material.

2. The electromedical implant according to claim 1, wherein the electromedical implant is a neurostimulation implant in the form of a spinal cord stimulation device, a vagus nerve stimulation device, or a brain stimulation device or as a muscle stimulation device, or as a cardiac implant in the form of a sensor, a monitoring device, a pacemaker device, a pacemaker device having an integrated defibrillator function, or a pacemaker device without intracardiac electrodes.

3. The electromedical implant according to claim 1, wherein the housing segment A and/or the housing segment C comprise a coating made of an electrically insulating material, and wherein the housing segment .A and/or the housing segment C comprise at least one region having no coating made of the electrically insulating material.

4. The electromedical implant according to claim 1, wherein the electrical feedthrough is made of a multilayer technology material.

5. The electromedical implant according to claim 1, wherein the electromedical implant further comprises at least one active or passive component, which is integrated in the feedthrough or joined to the feedthrough.

6. The electromedical implant according to claim 1, wherein the electromedical implant comprises an antenna, which is integrated in the feedthrough or joined to the feedthrough.

7. The electromedical implant according to claim 1, wherein the housing segment A is joined to the housing segment B or wherein the housing segment B is joined to the housing segment C via a low-temperature solder joint, a laser solder joint, a cold weld joint, a friction Weld joint, a fusion weld joint, an ultrasonic weld joint, or an adhesive joint.

8. The electromedical implant according to claim 1, wherein the electrical feedthrough has a composition comprising multiple layers, the multiple layers being alternately made of electrically insulating material and an electrically conducting material, such that at least the first electrical conductor extends directly through multiple layers of the electrically insulating material and multiple layers of the electrically conducting material.

9. The electromedical implant according to claim 1, wherein the conductor start of the first electrical conductor is connected to a. first input of an operational amplifier that feeds into the electric circuit arrangement and the conductor start of the second electrical conductor is connected to a second input of the operational amplifier.

10. A method for producing an electromedical implant, the method comprising:
    providing an electronics module comprising an electric circuit arrangement to pickup and further process electrical signals, the electronics module having at least two electrical conductors for measuring electrical potentials;
    providing a battery module,
    providing a single electrical feedthrough, the electrical feedthrough being at least partially made of an electrically insulating material;
    providing a housing shell A and a housing shell C, the housing shells A and C being at least partially made of electrically conducting material;
    arranging the feedthrough between the electronics module and the battery module;
    establishing an electrical connection between the electronics module and the battery module via the feedthrough;
    establishing an electrical connection between the electric circuit arrangement and a portion of the housing shell A made of electrically conducting material;
    establishing an electrical connection between the electric circuit arrangement and a portion of the housing shell C made of the electrically conducting material via the feedthrough;
    attaching the housing shell A on a first side of the feedthrough located towards the electronics module so that the electronics module is arranged within the housing shell A and is hermetically sealed: and
    attaching the housing shell C on a second side of the feedthrough located towards the battery module so that the battery module is arranged within the housing shell. C and is hermetically sealed,
    wherein the housing shell A and the housing shell C are electrically insulated from one another by the feedthrough.

11. The method for producing an electromedical implant according to claim 10, wherein the electromedical implant is a cardiac implant in the form of a. sensor, a monitoring device, a pacemaker device, a pacemaker device having an integrated defibrillator function, or a pacemaker device without intracardiac electrodes.

12. The method for producing an electromedical implant according to claim 10, further comprising:
    coating the housing shell A and/or the housing shell C with an electrically insulating material, a region of the housing shell A and/or of the housing shell. C not being coated by the electrically insulating material.

13. The method for producing an electromedical implant according to claim 10, wherein the attaching of housing shell A and/or the housing shell C is performed by low-temperature soldering, laser soldering, cold welding, friction welding, fusion welding, ultrasonic welding, or gluing.

14. The method for producing an electromedical implant -cording to claim 10, further comprising:
    integrating at least one passive or active component and/or an antenna in the feedthrough.

15. The method for producing an electromedical implant according to claim 10, wherein the electrical feedthrough has a composition comprising multiple layers, the multiple layers being alternately made of an electrically insulating material and an electrically conducting material, such that at least one electrical conductor that extends through the electrical feedthrough extends directly through multiple layers of the electrically insulating material and multiple layers of the electrically conducting material.

16. The method for producing an electromedical implant according to claim 10, wherein housing shell A and/or housing shell C are formed of two joined half shells.

* * * * *